(12) United States Patent
Han et al.

(10) Patent No.: US 11,066,683 B2
(45) Date of Patent: *Jul. 20, 2021

(54) RECOMBINANT CORYNEBACTERIUM CAPABLE OF PRODUCING BILIVERDIN IX-ALPHA AND METHOD OF PRODUCING BILIVERDIN IX-ALPHA USING THE SAME

(71) Applicant: Korea University Research and Business Foundation, Seoul (KR)

(72) Inventors: Sung Ok Han, Seoul (KR); Jiho Seok, Seoul (KR); Young-jin Ko, Chuncheon-si (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/849,086

(22) Filed: Apr. 15, 2020

(65) Prior Publication Data
US 2020/0377915 A1 Dec. 3, 2020

(30) Foreign Application Priority Data
May 31, 2019 (KR) .................. 10-2019-0064587

(51) Int. Cl.
| | |
|---|---|
| C12N 1/21 | (2006.01) |
| C12N 9/02 | (2006.01) |
| C12N 9/90 | (2006.01) |
| C12P 17/16 | (2006.01) |
| C12N 1/20 | (2006.01) |

(52) U.S. Cl.
CPC ............. *C12P 17/165* (2013.01); *C12N 1/20* (2013.01); *C12N 9/0008* (2013.01); *C12N 9/0083* (2013.01); *C12N 9/90* (2013.01); *C12N 9/001* (2013.01); *C12Y 102/0107* (2013.01); *C12Y 103/98* (2013.01); *C12Y 114/99003* (2013.01); *C12Y 504/03008* (2013.01)

(58) Field of Classification Search
None
See application file for complete search history.

(56) References Cited

U.S. PATENT DOCUMENTS

| | | | | |
|---|---|---|---|---|
| 2014/0038295 A1* | 2/2014 | Takemoto | .............. | C12N 15/70 435/471 |

FOREIGN PATENT DOCUMENTS

| | | |
|---|---|---|
| KR | 10-1756338 B1 | 7/2017 |
| KR | 10-1780767 B1 | 9/2017 |
| KR | 10-2018-0127239 A | 11/2018 |

OTHER PUBLICATIONS

Ko et al., Corynebacterium glutamicum Uses Coproporphyrin-dependent Pathway for Heme Metabolism Instead of Protoporphyrin-dependent Branch, Korean Society of Biological Engineering Conference 2018 [Abstract] Apr. 2018, p. 306. (Year: 2018).*
Seok et al., Engineering the Push and Pull of Biliverdin Biosynthesis via Protoporphyrin Independent Pathway in Corynebacterium glutamicum, Korean Society of Biological Engineering Conference 2018 [Abstract] Apr. 2018, p. 304. (Year: 2018).*
Dailey et al, HemQ: An iron-coproporphyrin oxidative decarboxylase for protoheme synthesis in Firmicutes and Actinobacteria, Archives Biochem. Biophys. 574, 2015, 27-35. (Year: 2015).*
Uniprot, Accession No. A0A1Q3DR23, 2017, www.uniprot.org. (Year: 2017).*
Yu et al., Engineering Corynebacterium glutamicum to produce 5-aminolevulinic acid from glucose, Microb. Cell. Fact. 14, 2015, 183. (Year: 2015).*
Choi et al., Heme Derived from Corynebacterium glutamicum, J. Microbiol. Biotechnol. 27, 2017, 500-06. (Year: 2017).*
Baritugo et al., Metabolic engineering of Corynebacterium glutamicum for fermentative production of chemicals in biorefinery, Appl. Microbiol. Biotechnol. 102, 2018, 3915-37. (Year: 2018).*
Ramzi et al., 5-Aminolevulinic acid production in engineered Corynebacteriumglutamicum via C5 biosynthesis pathway, Enz. Microbial. Technol. 81, 2015, 1-7. (Year: 2015).*
Gene amplification, IUPAC. Compendium of Chemical Terminology, 2nd ed. (the "Gold Book"), Blackwell Scientific Publications, Oxford (1997), doi.org/10.1351/goldbook.G02605 (Year: 1997).*
Wang et al., A mutant HemA protein with positive charge close to the N terminus is stabilized against heme-regulated proteolysis in *Salmonella typhimurium*, J Bacteriol. 181, 1999, 6033-41. (Year: 1999).*
Choby et al., "Heme Synthesis and Acquisition in Bacterial Pathogens," Journal of Molecular Biology, Nov. 28, 2016, vol. 428, No. 17, pp. 3408-3428.
Wegele et al., "The Heme Oxygenase(s)-Phytochrome System of Pseudomonas aeruginosa," The Journal of Biological Chemistry, Aug. 15, 2004, vol. 279, No. 44, pp. 45791-45802.
Bulmer et al., "The anti-mutagenic properties of bile pigments," Mutation research Reviews in mutation research, 658, 2008, pp. 28-41.
McPhee et al., "Bile pigments as HIV-1 protease inhibitors and their effects on HIV-1 viral maturation and infectivity in vitro," The Biochemical Journal. 320, 1996, pp. 681-686.
Ohrui et al., "Transient Relief of Asthma Symptoms during Jaundice: A Possible Beneficial Role of Bilirubin," The Tohoku Journal of Experimental Medicine, 199, 2003, pp. 193-196.

(Continued)

*Primary Examiner* — Robert B Mondesi
*Assistant Examiner* — Todd M Epstein
(74) *Attorney, Agent, or Firm* — NSIP Law

(57) ABSTRACT

Disclosed are recombinant strain of a genus *Corynebacterium* capable of producing biliverdin IX-alpha (IXα) and a method of producing biliverdin IX-alpha using the same. The recombinant strain is capable of synthesizing biliverdin IX-alpha in an environmentally friendly manner using only glucose without the addition of any nitrogen source, thus replacing the synthesis of biliverdin IX-alpha through chemical treatment, which is a conventional synthetic method causing environmental pollution problems.

4 Claims, 5 Drawing Sheets

Specification includes a Sequence Listing.

(56) References Cited

OTHER PUBLICATIONS

Seok et al., "Systems metabolic engineering of Corynebacterium glutamicum for the bioproduction of biliverdin via protoporphyrin independent pathway," Journal of Biological Engineering, 2019, 13 pages.

* cited by examiner

SEQUENCE LISTING

<160> NUMBER OF SEQ ID NOS: 24

<210> SEQ ID NO 1
<211> LENGTH: 1263
<212> TYPE: DNA
<213> ORGANISM: Salmonella typhimurium

<400> SEQUENCE: 1

| | | | | | |
|---|---|---|---|---|---|
| atgaccaaga | agcttttagc | gctcggtatt | aaccataaaa | cggcacctgt | atcgctgcga | 60 |
| gaacgcgtaa | cgttttcgcc | ggacacgctt | gatcaggcgc | tggacagcct | gcttgcgcag | 120 |
| ccaatggtgc | agggcggggt | cgtgctgtca | acctgtaacc | gtacagagct | gtatctgagc | 180 |
| gtggaagagc | aggataacct | gcaagaagcg | ctgatccgct | ggttatgcga | ttaccataac | 240 |
| ctgaacgagg | acgatctgcg | caacagtctg | tactggcatc | aggacaatga | cgccgtcagc | 300 |
| cacctgatgc | gcgtcgccag | cggtctggat | tcactggtgc | tgggcgaacc | gcaaatcctc | 360 |
| ggtcaggtga | aaaagcgtt  | tgcggattcg | caaaaaggcc | accttaacgc | cagcgcgctg | 420 |
| gagcgaatgt | ttcagaagtc | ttttccgtc  | gctaagcgag | tgcggactga | aaccgatatc | 480 |
| ggcgctagcg | ccgtctccgt | cgcgtttgcc | gcctgtacgc | tcgcccgcca | aatctttgaa | 540 |
| tcgctctcga | cggtcaccgt | actgttagtt | ggcgcgggcg | aaaccattga | actggtggcg | 600 |
| cgtcacctgc | gcgagcataa | agtacaaaag | atgattatcg | ccaaccgaac | ccgcgagcgc | 660 |
| gcgcaagccc | tggcggatga | ggtaggcgct | gaggttatct | cgctcagcga | tatcgacgcc | 720 |
| cgtttgcagg | atgccgatat | tattatcagt | tcgaccgcca | gcccgctgcc | gattatcggt | 780 |
| aaaggcatgg | tggagcgcgc | attaaaaagc | cgtcgcaacc | agccgatgct | gctggtggat | 840 |
| attgccgtac | cgcgcgacgt | tgaaccggaa | gtcggcaaac | tggcgaacgc | ttatctttat | 900 |
| agcgtcgatg | atttacagag | catcatttcg | cataatctgg | cgcagcgtca | ggctgcggca | 960 |
| gtagaagcgg | aaacgattgt | tgagcaggaa | gccagcgagt | ttatggcctg | gctacgcgcc | 1020 |
| caggggcca  | gcgagaccat | tcgggaatac | cgtagtcagt | cggagcagat | tcgtgacgaa | 1080 |
| ctgactacca | aagcgctgtc | ggcccttcaa | cagggcggtg | atgcgcaagc | catcttgcag | 1140 |
| gatctggcat | ggaaactgac | caaccgcctg | attcatgcgc | aacgaaatc  | acttcaacag | 1200 |
| gctgcccgtg | acggggatga | cgaacgcctg | aatattctgc | gcgacagcct | cgggctggag | 1260 |
| tag | | | | | | 1263 |

<210> SEQ ID NO 2
<211> LENGTH: 1281
<212> TYPE: DNA
<213> ORGANISM: Escherichia coli

<400> SEQUENCE: 2

| | | | | | |
|---|---|---|---|---|---|
| atgagtaagt | ctgaaaatct | ttacagcgca | gcgcgcgagc | tgatccctgg | cggtgtgaac | 60 |
| tcccctgttc | gcgcctttac | tggcgtgggc | ggcactccac | tgtttatcga | aaaagcggac | 120 |
| ggcgcttatc | tgtacgatgt | tgatggcaaa | gcctatatcg | attatgtcgg | ttcctggggg | 180 |
| ccgatggtgc | tgggccataa | ccatccggca | tccgcaatg  | ccgtgattga | agccgccgag | 240 |
| cgtggtttaa | gctttggtgc | accaaccgaa | atggaagtga | aaatggcgca | actggtgact | 300 |
| gaactggtcc | cgaccatgga | tatggtgcgc | atggtgaact | ccggcaccga | ggcgacgatg | 360 |
| agcgccatcc | gcctggccgc | tggttttacc | ggtcgcgaca | aaattattaa | atttgaaggt | 420 |
| tgttaccacg | gtcacgctga | ctgcctgctg | gtgaaagccg | gttctggcgc | actcacgtta | 480 |
| ggccagccaa | actcgccggg | cgttccggca | gatttcgcca | acatacctt  | aacctgtact | 540 |

-continued

| | |
|---|---|
| tataacgatc tggcttctgt acgcgccgcg tttgagcaat acccgcaaga gattgcctgt | 600 |
| attatcgtcg agccggtggc aggcaatatg aactgcgttc caccgctgcc agagttcctg | 660 |
| ccaggtctgc gtgcgctgtg cgacgaattt ggcgcattgc tgatcatcga tgaagtaatg | 720 |
| accggcttcc gcgtggcact ggctggcgca caggattatt acggtgtgga accggatctc | 780 |
| acctgcctgg gcaaaatcat cggcggtgga atgccggtag gcgcattcgg tggtcgtcgt | 840 |
| gatgtaatgg atgcgctggc cccgacgggt ccggtctatc aggcgggtac gctttccggt | 900 |
| aacccaattg cgatggcagc gggtttcgcc tgtctgaatg aagtcgcgca gccgggcgtt | 960 |
| cacgaaacgt tggatgagct gacatcacgt ctggcagaag gtctgctgga agcggcagaa | 1020 |
| gaagccggaa ttccgctggt cgttaaccac gttggcggca tgttcggtat tttctttacc | 1080 |
| gacgccgagt ccgtgacgtg ctatcaggat gtgatggcct gtgacgtgga acgctttaag | 1140 |
| cgtttcttcc atatgatgct ggacgaaggt gtttacctgg caccgtcagc gtttgaagcg | 1200 |
| ggctttatgt ccgtggcgca cagcatggaa gatatcaata acaccatcga tgctgcacgt | 1260 |
| cgggtgtttg cgaagttgtg a | 1281 |

<210> SEQ ID NO 3
<211> LENGTH: 699
<212> TYPE: DNA
<213> ORGANISM: Corynebacterium glutamicum

<400> SEQUENCE: 3

| | |
|---|---|
| atgagcgagc tcgatattaa acagctcaac aaactgcagc gctactctca gtgggcggtg | 60 |
| ttccgtgcta ttcctggagc gctcgatgat gatcgcacag aagtcactga ccaagcagcc | 120 |
| aagttctttg ccgaccttga agcagaaggc aaagtcactg tccgtggcat ttacaacgcc | 180 |
| tccggcctgc gcgcagacgc tgactacatg atctggtggc acgcagaaga attcgaagac | 240 |
| attcagaagg ccttcgctga tttccgccgc accaccattt gggtcaggt ttctgaggtc | 300 |
| ttctggatcg gaaacgctct ccaccgtcca tctgagttca caaggctca cttgccttca | 360 |
| ttcatcatgg gtgaagaagc aaaggactgg atcactgttt acccgttcgt gcgcagctac | 420 |
| gactggtaca tcatggagcc cttgaagcgt tcccgcattc tccgcgagca cggacaagct | 480 |
| gctgtggaat tcccagatgt tcgtgccaac actgtgccgg ctttcgcact gggtgactac | 540 |
| gaatgggtgc tggctttcga ggctgatgag ttgcaccgca ttgtcgattt gatgcacaag | 600 |
| atgcgttaca ccgaggctcg cctccacgtc cgtgaggagc tgccatttat ttctggacag | 660 |
| cgcgtcgaca ttgcagatct gattaaggtt cttccttaa | 699 |

<210> SEQ ID NO 4
<211> LENGTH: 648
<212> TYPE: DNA
<213> ORGANISM: Corynebacterium glutamicum

<400> SEQUENCE: 4

| | |
|---|---|
| atgacaagca ttattgcaag caacagcgac ctatcggagg cgctgcgcac ccacactgcg | 60 |
| caggcccatg aagaggccga gcactcaacg tttatgaatg atctgctcac cgggaagctc | 120 |
| gatgcgcagg catttatcaa gttgcaggag caatcatggt tgttctacac cgctttggaa | 180 |
| gctgcagctc gtgcatgtgc agaggattcc cgtgcggctg gtctgctgga cccacgcctc | 240 |
| gagcgcaagg aaacgttgga agctgatctg gataagctgc acgaaaacac cacctggcgt | 300 |
| gacaacgtca cggccactgc agcgacagcg tcttatgtgg aacgtcttga aagcatcgaa | 360 |

```
gcggccaagg atttccctcg tttggttgct catcactatg tccgctacct gggtgatttg        420
tccggtgggc aggttattgc acgtctggtg aacagggaat atggagtttc ggaagaggcg        480
ttgagcttct actgctttga agatcttggc aagctcaaac cgtacaagga taattaccgt        540
gcagagcttg atgctttgga attaacagca gaggagcgtg ctgcgttgct ggatgaagca        600
tctgatgcgt tcaggtttaa tcagcaagtt tttcaggctc ttgcttaa                    648

<210> SEQ ID NO 5
<211> LENGTH: 1143
<212> TYPE: DNA
<213> ORGANISM: Corynebacterium glutamicum

<400> SEQUENCE: 5
atgtcagttt ttggtgtgta tattcatgtg ccgttttgtt caactcggtg cggttattgc         60
gatttcaaca cctatactgc tggggaatta ggtagtactg caggcccgga cacctatctt        120
gactcgttgg aagttgagtt ggagatggct gtggcttcgc tggataatcc tcggcaggcg        180
gaaactatct ttattggcgg gggtaccccg tcgttgattg gtgcggacgg tttggccagg        240
gttttggggg ctgtgcgcaa tactttggc attgcggatg gtgcggaagt caccacggag         300
tccaatccgg agtctacctc gcctgagttt ttcgatggcc tgcgtgaggc gggctacaac        360
aggatttcgt tagggatgca gtcggcgtcg tcaagcgttt tgaaggtgct ggaccgcacg        420 cacccccag ggcgcccggt ggcggcggcc aaggaggcac gtgaggcggg gtttgagcat        480
gtcaatttgg acatgattta tggcacgccg acagagaccg atgatgatgt ccgcaagacg        540
ctggatgcgt tgctcgaagc gaacgtggat cacgtgtctg cctattcctt gatcgtggaa        600
gatggcacgg cgatggcgcg caaggtgcgc aagggcgagc tgccagcgcc ggacgaggat        660
gtctacgctg atcgttttga gcttatcgac gctcgcctgc gctcagctgg tttcgattgg        720
tacgaggtgt ccaactgggc gaaacccggc ggagaatgca agcacaacat gggctattgg        780
gtcgacggcg actggtgggg cgcggggccc ggcgcgcact cgcacatcgg cgaccgccgc        840
ttctacaaca tcaagcaccc agcgcgttac tccgcgcaga ttgcggccgg cgagctgccc        900
attaaggaaa cagagcggct gacggcggaa gatcaccaca ccgagcgcgt catgcttggt        960
ttgcgcctga acaaggcgt gccgctgaac cttttcgcac ccgcagcgcg cccggtcatc       1020
gaccgtcata tcgcaggggg cctgctgcac gtcaatgcgc tgggcaacct ggcggtgacc      1080
gatgcgggac gtttgcttgc cgacggcatc atcgccgaca ttttgcttag tgaagaagac      1140
taa                                                                    1143

<210> SEQ ID NO 6
<211> LENGTH: 375
<212> TYPE: DNA
<213> ORGANISM: Artificial Sequence
<220> FEATURE:
<223> OTHER INFORMATION: Zeocin resistant gene

<400> SEQUENCE: 6
atggccaagt tgaccagtgc cgttccggtg ctcaccgcgc gcgacgtcgc cggagcggtc         60
gagttctgga ccgaccggct cgggttctcc cggacttcg tggaggacga cttcgccggt        120
gtggtccggg acgacgtgac cctgttcatc agcgcggtcc aggaccaggt ggtgccggac        180
aacaccctgg cctgggtgtg ggtgcgcggc ctggacgagc tgtacgccga gtggtcggag        240
gtcgtgtcca cgaacttccg ggacgcctcc gggccggcca tgaccgagat cggcgagcag        300
ccgtgggggc gggagttcgc cctgcgcgac ccggccggca actgcgtgca cttcgtggcc        360
```

```
gaggagcagg actga                                                    375

<210> SEQ ID NO 7
<211> LENGTH: 43
<212> TYPE: DNA
<213> ORGANISM: Artificial Sequence
<220> FEATURE:
<223> OTHER INFORMATION: primer

<400> SEQUENCE: 7
aatctgcaga aggagatata catgaccaag aagcttttag cgc                      43

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
actgtcgact cacaacttcg caaacaccc                                      29

<210> SEQ ID NO 9
<211> LENGTH: 33
<212> TYPE: DNA
<213> ORGANISM: Artificial Sequence
<220> FEATURE:
<223> OTHER INFORMATION: primer

<400> SEQUENCE: 9
cccgtcgacg ttgacaatta atcatcggca tag                                 33

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
attacgtagt gtcagtcctg ctcctc                                         26

<210> SEQ ID NO 11
<211> LENGTH: 34
<212> TYPE: DNA
<213> ORGANISM: Artificial Sequence
<220> FEATURE:
<223> OTHER INFORMATION: primer

<400> SEQUENCE: 11
gggatcgata tgtcagtttt tggtgtgtat attc                                34

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
cccgcggccg cttagtcttc ttcactaagc aaaatg                              36

<210> SEQ ID NO 13
<211> LENGTH: 33
<212> TYPE: DNA
```

-continued

<213> ORGANISM: Artificial Sequence
<220> FEATURE:
<223> OTHER INFORMATION: primer

<400> SEQUENCE: 13
cccatcgata tgagcgagct cgatattaaa cag                          33

<210> SEQ ID NO 14
<211> LENGTH: 42
<212> TYPE: DNA
<213> ORGANISM: Artificial Sequence
<220> FEATURE:
<223> OTHER INFORMATION: primer

<400> SEQUENCE: 14
ccagcggccg cttaaggaag aaccttaatc agatctgcaa tg               42

<210> SEQ ID NO 15
<211> LENGTH: 30
<212> TYPE: DNA
<213> ORGANISM: Artificial Sequence
<220> FEATURE:
<223> OTHER INFORMATION: primer

<400> SEQUENCE: 15
gcgatcgata tgacaagcat tattgcaagc                              30

<210> SEQ ID NO 16
<211> LENGTH: 39
<212> TYPE: DNA
<213> ORGANISM: Artificial Sequence
<220> FEATURE:
<223> OTHER INFORMATION: primer

<400> SEQUENCE: 16
gggggatcct taagcaagag cctgaaaaac ttgctgatt                    39

<210> SEQ ID NO 17
<211> LENGTH: 45
<212> TYPE: DNA
<213> ORGANISM: Artificial Sequence
<220> FEATURE:
<223> OTHER INFORMATION: primer

<400> SEQUENCE: 17
gccggatcca aggagatata gatgagcgag ctcgatatta aacag             45

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
cgcggtacct taaggaagaa ccttaatcag atctgc                       36

<210> SEQ ID NO 19
<211> LENGTH: 47
<212> TYPE: DNA
<213> ORGANISM: Artificial Sequence
<220> FEATURE:
<223> OTHER INFORMATION: primer

<400> SEQUENCE: 19
cccggatcca aggagatata gatgacaagc attattgcaa gcaacag           47

```
<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
cccggtacct taagcaagag cctgaaaaac ttgctg                                 36

<210> SEQ ID NO 21
<211> LENGTH: 46
<212> TYPE: DNA
<213> ORGANISM: Artificial Sequence
<220> FEATURE:
<223> OTHER INFORMATION: primer

<400> SEQUENCE: 21
cccgcggccg caaggagata tagatgacaa gcattattgc aagcaa                      46

<210> SEQ ID NO 22
<211> LENGTH: 35
<212> TYPE: DNA
<213> ORGANISM: Artificial Sequence
<220> FEATURE:
<223> OTHER INFORMATION: primer

<400> SEQUENCE: 22
gaggcggccg cttaagcaag agcctgaaaa acttg                                  35

<210> SEQ ID NO 23
<211> LENGTH: 46
<212> TYPE: DNA
<213> ORGANISM: Artificial Sequence
<220> FEATURE:
<223> OTHER INFORMATION: primer

<400> SEQUENCE: 23
cccggatcca aggagatata gatgagcgag ctcgatatta aacagc                      46

<210> SEQ ID NO 24
<211> LENGTH: 43
<212> TYPE: DNA
<213> ORGANISM: Artificial Sequence
<220> FEATURE:
<223> OTHER INFORMATION: primer

<400> SEQUENCE: 24
ggggcggccg cttaaggaag aaccttaatc agatctgcaa tgt                         43
```

RECOMBINANT CORYNEBACTERIUM CAPABLE OF PRODUCING BILIVERDIN IX-ALPHA AND METHOD OF PRODUCING BILIVERDIN IX-ALPHA USING THE SAME

CROSS-REFERENCE TO RELATED APPLICATION

This application claims the benefit under 35 USC 119(a) of Korean Patent Application No. 10-2019-0064587 filed on May 31, 2019, in the Korean Intellectual Property Office, the entire disclosures of which are incorporated herein by reference for all purposes.

INCORPORATION-BY-REFERENCE OF MATERIAL SUBMITTED BY U.S.P.T.O. EFS-WEB

The instant application contains a Sequence Listing which is being submitted in computer readable form via the United States Patent and Trademark Office eFS-WEB system and which is hereby incorporated by reference in its entirety for all purposes. The txt file submitted herewith contains a 12 KB file (NewApp_0181650013_SequenceListing.txt).

BACKGROUND OF THE INVENTION

Field of the Invention

The present invention relates to recombinant *Corynebacterium* capable of producing biliverdin IX-alpha (IXα) and a method of producing biliverdin IX-alpha using the same, and more particularly to a recombinant strain of the genus *Corynebacterium* with improved heme biosynthesis capability, characterized in that a gene hemA, encoding a glutamyl-tRNA reductase, a gene hemL, encoding a glutamate-1-semialdehyde aminotransferase, and a gene hemQ, encoding an Fe-coproporphyrin III decarboxylase, are amplified, wherein the gene hmuO encoding a heme oxygenase is further amplified and the recombinant strain of the genus *Corynebacterium* has the capacity to produce biliverdin IX-alpha, and a method of producing biliverdin IX-alpha using the same.

Description of the Related Art

Biliverdin is a green bile pigment contained in the bile of herbivores. Hemoglobin in red blood cells is hydrolyzed and broken down into heme and globin, and heme is oxidatively cleaved to biliverdin, which is reduced to bilirubin, in the reticuloendothelial cell.

Biliverdin is found in the blood of patients with liver disease, and biliverdin or bilirubin accumulates in circulatory tissues, causing jaundice. Biliverdin is considered to be a simple byproduct that is normally formed during the breakdown of heme, but there is evidence that biliverdin and other bile pigments perform physiological functions (Bulmer, A C et al., *Mutation Research*. 658:28~41, 2008).

Bile pigments such as biliverdin can perform useful physiological functions due to the antimutagenic and antioxidant activities thereof, and biliverdin and bilirubin are known to be potent removers of peroxy radicals (Bulmer, A C et al., *Mutation Research.*, 658:28~41, 2008). These have been found to suppress the activities of mutagens such as polycyclic aromatic hydrocarbons, heterocyclic amines and oxidants, and some studies have reported that people with high concentrations of bilirubin and biliverdin in their bodies have lower incidence of cancer and cardiovascular diseases. Biliverdin has been suggested to act as HIV-1 protease inhibitors, as well as many different tetrapyrrolic dyes, and to have beneficial effects on asthma (McPhee, F. et al., The Biochemical Journal. 320 (Pt 2): 681~6, 1996; Ohrui, T et al., The Tohoku Journal of Experimental Medicine. 199: 193~6, 2003).

Recently, demand for biliverdin IX-alpha has increased as the necessity therefor increases in various fields such as those of antioxidant drugs, optogenetic precursors and pigment precursors. In the case of conventional biliverdin IX-alpha, it has been produced by chemical oxidation of bilirubin extracted from the bile of mammals, but this method not only causes problems due to the use of animal-derived raw materials but also environmental problems due to impurities contained therein. The production technology for biliverdin IX-alpha through the fermentation of *Escherichia coli* requires the continuous addition of a nitrogen source and has a disadvantage of low synthesis yield.

Accordingly, as a result of intensive efforts to develop a method for producing biliverdin IX-alpha in high yield without the concern of contamination of animal-derived raw materials, the present inventors have found that, when the genes involved in the rate determination of the metabolic pathway for producing biliverdin IX-alpha using *Corynebacterium glutamicum* are selected and overexpressed, biliverdin IX-alpha can be produced in high yield without the addition of a nitrogen source while minimizing the metabolic burden on the microorganism. Based on this finding, the present invention has been completed.

SUMMARY OF THE INVENTION

Therefore, the present invention has been made in view of the above problems, and it is one object of the present invention to provide a recombinant strain of the genus *Corynebacterium* capable of producing biliverdin IX-alpha.

It is another object of the present invention to provide a method of producing biliverdin IX-alpha using the recombinant strain of the genus *Corynebacterium* capable of producing biliverdin IX-alpha.

It is another object of the present invention to provide a recombinant strain of the genus *Corynebacterium* with increased heme biosynthesis capability.

It is another object of the present invention to provide a method of producing heme using the recombinant strain of the genus *Corynebacterium* with increased heme biosynthesis capability.

In accordance with an aspect of the present invention, the above and other objects can be accomplished by the provision of a recombinant strain of the genus *Corynebacterium* with improved heme biosynthesis capability, characterized in that a gene hemA, encoding a glutamyl-tRNA reductase, a gene hemL, encoding a glutamate-1-semialdehyde aminotransferase, and a gene HemQ, encoding an Fe-coproporphyrin III decarboxylase, are amplified.

There is provided a recombinant strain of the genus *Corynebacterium* with the capacity to produce biliverdin IX-alpha, characterized in that a gene hmuO, encoding a heme oxygenase, is further amplified in the recombinant strain of the genus *Corynebacterium* with improved heme biosynthesis capability.

In accordance with another aspect of the present invention, there is provided a method of producing a heme including (a) producing a heme by culturing the recombinant strain of the genus *Corynebacterium* with improved heme biosynthesis capability, and (b) recovering the produced heme.

In accordance with another aspect of the present invention, there is provided a method of producing biliverdin IX-alpha including (a) producing biliverdin IX-alpha by culturing the recombinant strain of the genus *Corynebacterium* capable of producing biliverdin IX-alpha, and (b) recovering the produced biliverdin IX-alpha.

BRIEF DESCRIPTION OF THE DRAWINGS

The above and other objects, features and other advantages of the present invention will be more clearly understood from the following detailed description taken in conjunction with the accompanying drawings, in which.

Figure 5:
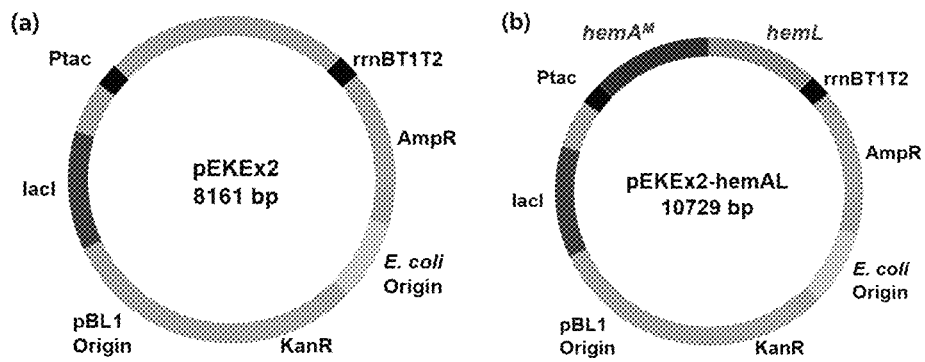
Figure 6:
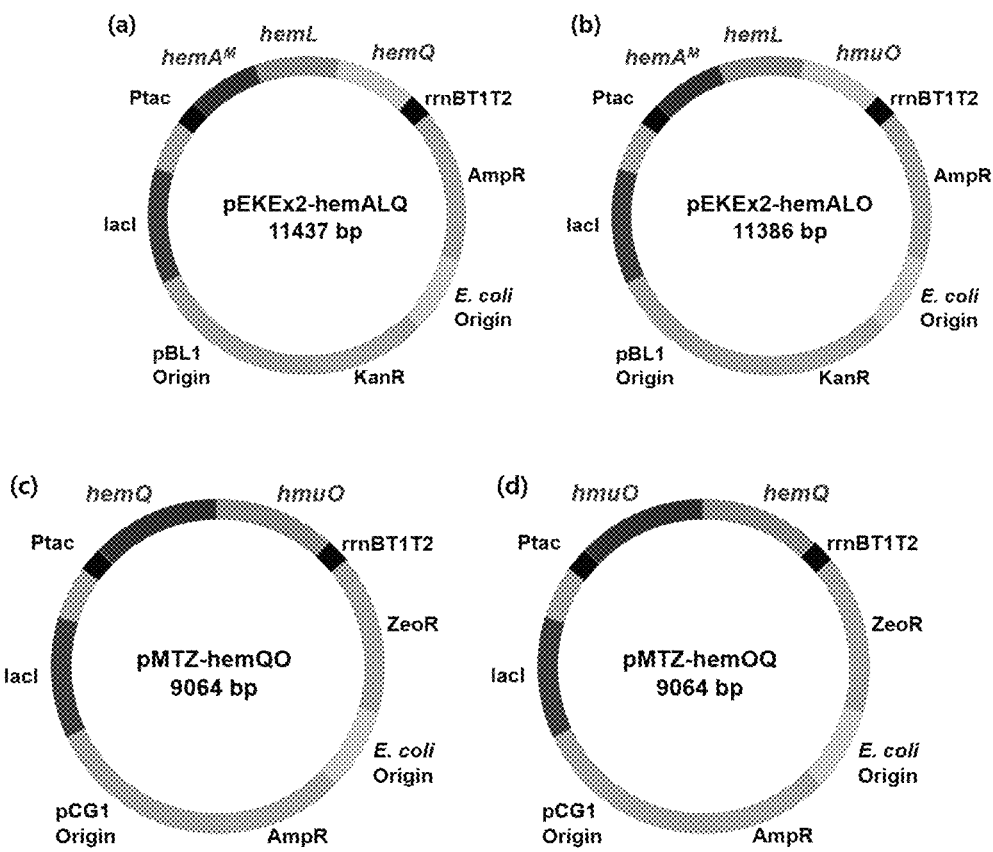
Figure 7:
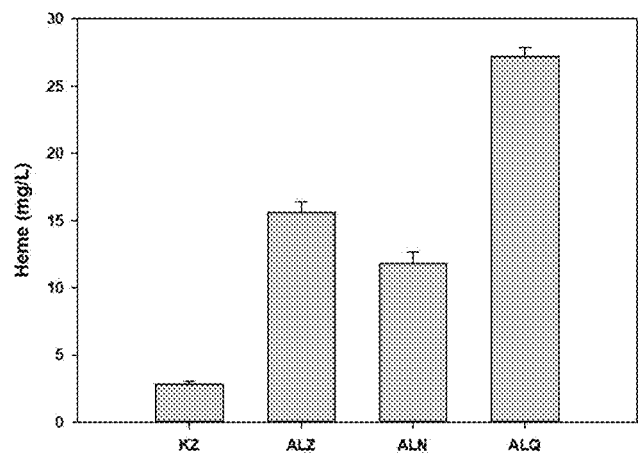
Figure 8:
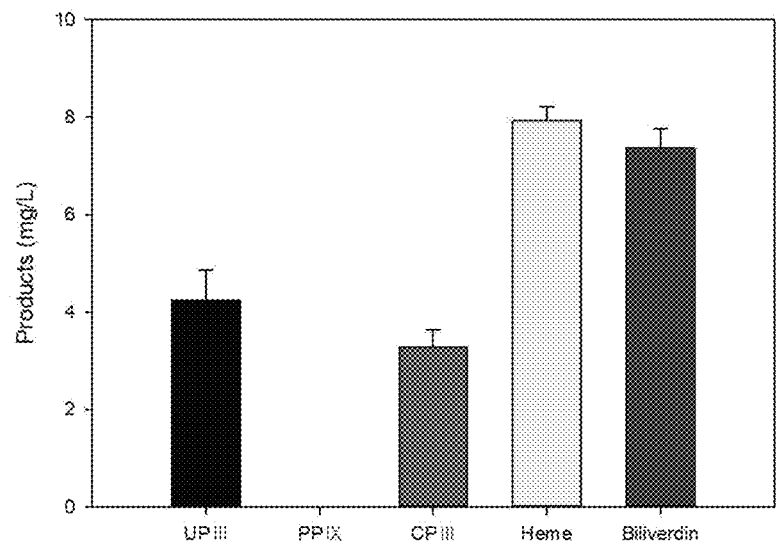
Figure 9:
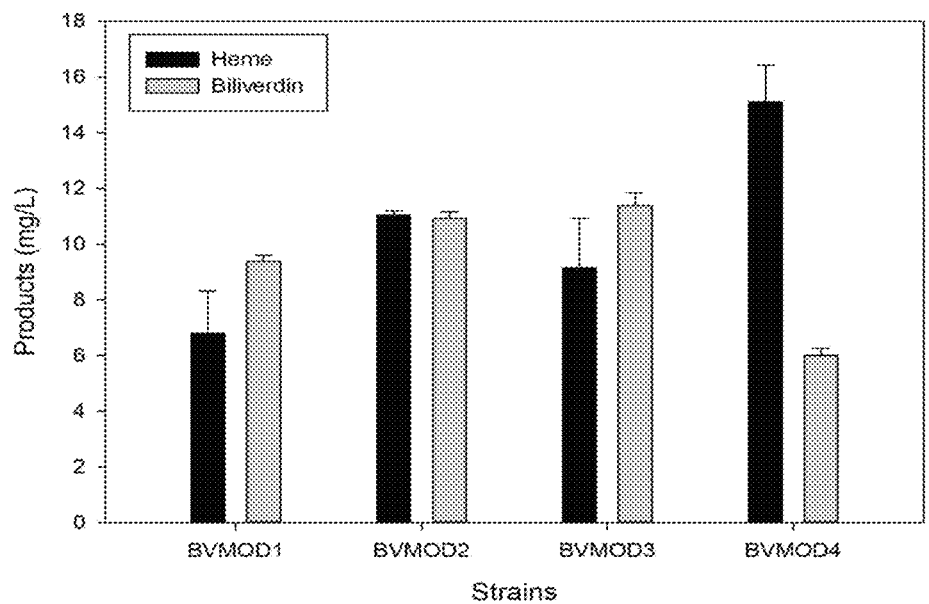
Figure 10:
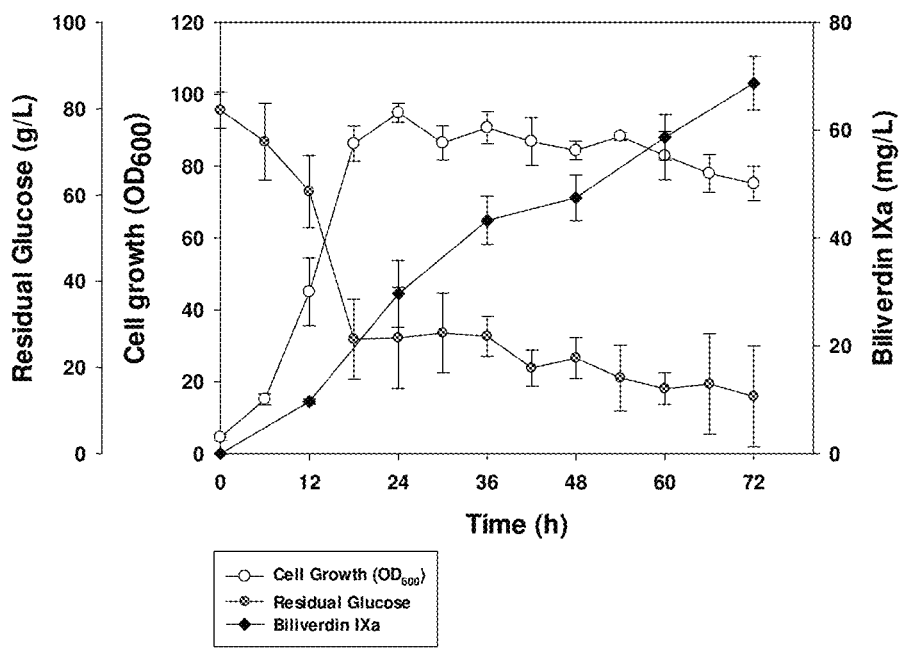

(a) and (b) of FIG. 5 show vector maps of a *Corynebacterium glutamicum* overexpression recombinant vector (pEKEx2) and a *Corynebacterium glutamicum* hemAL overexpression recombinant vector (pEKEx2-hemAL);

(a) to (d) of FIG. 6 show the structures of *Corynebacterium glutamicum* HemALQ, HemALO, HemQO and HemOQ overexpression recombinant vectors (pEKEx2-hemALQ, pEKEx2-hemALO, pMTZ-hemQO and pMTZ-hemOQ) and is a schematic diagram of *Corynebacterium glutamicum* recombinant strains (BVMOD1, BVMOD2, BVMOD3, BVMOD4) produced based on the vectors;

FIG. 7 shows the result of comparison in heme biosynthesis of *Corynebacterium glutamicum* recombinant strains (KZ, ALZ, ALN, ALQ);

FIG. 8 shows the result of a comparison of the biosynthesis of porphyrin byproducts such as uroporphyrin III, protoporphyrin IX and coproporphyrin III, and heme and biliverdin IX-alpha by *Corynebacterium glutamicum* recombinant strain ALO;

FIG. 9 shows the results of a comparison of the biosynthesis of heme and biliverdin IX-alpha by *Corynebacterium glutamicum* recombinant strains (BVMOD1, BVMOD2, BVMOD3, BVMOD4); and FIG. 10 shows the result of biosynthesis of biliverdin IX-alpha through fed-batch fermentation by *Corynebacterium glutamicum* recombinant strain BVMOD3.

DETAILED DESCRIPTION OF THE INVENTION

In the present invention, it was tried to develop a method of producing biliverdin IX-alpha at high yield using the *Corynebacterium glutamicum* recombinant strain overexpressing a glutamyl-tRNA reductase, a glutamate-1-semialdehyde aminotransferase and an Fe-coproporphyrin III decarboxylase, which is derived from *Corynebacterium glutamicum* strain and selected through in-vitro thermodynamic calculation. The recombinant strain efficiently synthesized heme, the precursor of biliverdin IX-alpha.

Therefore, in one aspect, the present invention is directed to a recombinant strain of the genus *Corynebacterium* with improved heme biosynthesis capability, characterized in that a gene hemA, encoding a glutamyl-tRNA reductase, a gene hemL, encoding a glutamate-1-semialdehyde aminotransferase, and a gene hemQ, encoding an Fe-coproporphyrin III decarboxylase, are amplified.

In the present invention, the strain may be characterized in that a recombinant vector including the hemA gene and the hemL gene, and a recombinant vector including HemQ are introduced.

In another aspect, the present invention is directed to a method of producing a heme including (a) producing heme by culturing the recombinant *Corynebacterium* strain with improved heme biosynthesis capability, and (b) recovering the produced heme.

In the present invention, further in-vitro thermodynamic calculation identified that the coproporphyrin III pathway is thermodynamically more stable than a conventional protoporphyrin-IX-related pathway. For comparison, recombinant strains overexpressing each of a coproporphyrinogen III oxidase (HemN), which is a coproporphyrin IX-related gene, and an Fe-coproporphyrin III decarboxylase (HemQ), which is a coproporphyrin III-related gene, along with hemA and hemL, were produced. The strain overexpressing HemA, HemL and HemN exhibited lower heme synthesis than the strain overexpressing HemA and HemL, but the strain overexpressing HemA, HemL and HemQ exhibited higher heme synthesis than the same. Therefore, a recombinant strain overexpressing a heme oxygenase (HmuO) along with a glutamyl-tRNA reductase (HemA) and glutamate-1-semialdehyde aminotransferase (HemL) was produced, and the biosynthesis of biliverdin IX-alpha by the recombinant strain was identified.

Therefore, in another aspect, the present invention is directed to a recombinant strain of the genus *Corynebacterium* having the capacity to produce biliverdin IX-alpha, characterized in that a hmuO gene, encoding a heme oxygenase, is further amplified in the recombinant strain of the genus *Corynebacterium* with improved heme biosynthesis capability.

In the present invention, the strain may be characterized in that a recombinant vector including a hemA gene and a hemL gene, and a recombinant vector including a hemQ gene and a hmuO gene are introduced.

In one embodiment of the present invention, strains that express all of a glutamyl-tRNA reductase, a glutamate-1-semialdehyde aminotransferase, a Fe-coproporphyrin III decarboxylase and a heme oxygenase, and thus exhibit the highest biliverdin IX-alpha synthesis yield through module optimization were identified, and the highest biliverdin IX-alpha yield was achieved through 5 L batch-culture fermentation.

In the present invention, the hemQ gene and hmuO gene are introduced in the form of hemQO by a recombinant vector.

The *Corynebacterium glutamicum* recombinant strain capable of producing biliverdin IX-alpha according to the present invention is a biologically produced strain that is capable of synthesizing biliverdin IX-alpha in an environmentally friendly manner using glucose without the addition of an additional nitrogen source, and is thus capable of replacing the synthesis of biliverdin IX-alpha through conventional chemical treatment.

In another aspect, the present invention is directed to a method of producing biliverdin IX-alpha comprising (a) producing biliverdin IX-alpha by culturing the recombinant *Corynebacterium* strain capable of producing biliverdin IX-alpha and (b) recovering the produced biliverdin IX-alpha.

In the present invention, the culture is capable of synthesizing biliverdin without adding an additional nitrogen source.

In one embodiment of the present invention, when the recombinant strain (BVMOD strain), in which the hemQO gene and the hemAL gene are introduced, is fed-batch cultured, the strain produced 70 mg/L of biliverdin IX-alpha in 72 hours.

In addition, the biliverdin-IX-alpha-producing recombinant strain developed according to the present invention is useful for a process for producing useful substances using the biliverdin-IX-alpha as a precursor such as bilirubin, phycoerythrobilin and phycocyanobilin, in addition to biliverdin IX-alpha (see FIG. 8).

Hereinafter, the present invention will be described in more detail with reference to examples. However, it will be obvious to those skilled in the art that these examples are provided only for illustration of the present invention and should not be construed as limiting the scope of the present invention.

Example 1: Thermodynamic Stability Analysis of Genes Related to Biliverdin IX-Alpha Synthesis Pathway in *Corynebacterium glutamicum*

In-vitro analysis was performed on the thermodynamic stability of genes involved in the biosynthetic pathway that produces biliverdin IX-alpha from L-glutamate in *Corynebacterium glutamicum*.

The analysis was conducted at 25° C., pH 7.3 and an ionic strength of 0.25M using a MetaCyc program (https://metacyc.org/). The change in Gibbs free energy in each reaction was calculated by subtracting the total Gibbs energy of the substrates from the total Gibbs energy of the product, and the value acquired in kcal/mol was converted to kJ/mol (1 kcal/mol=4.184 kJ/mol).

Figure 1:
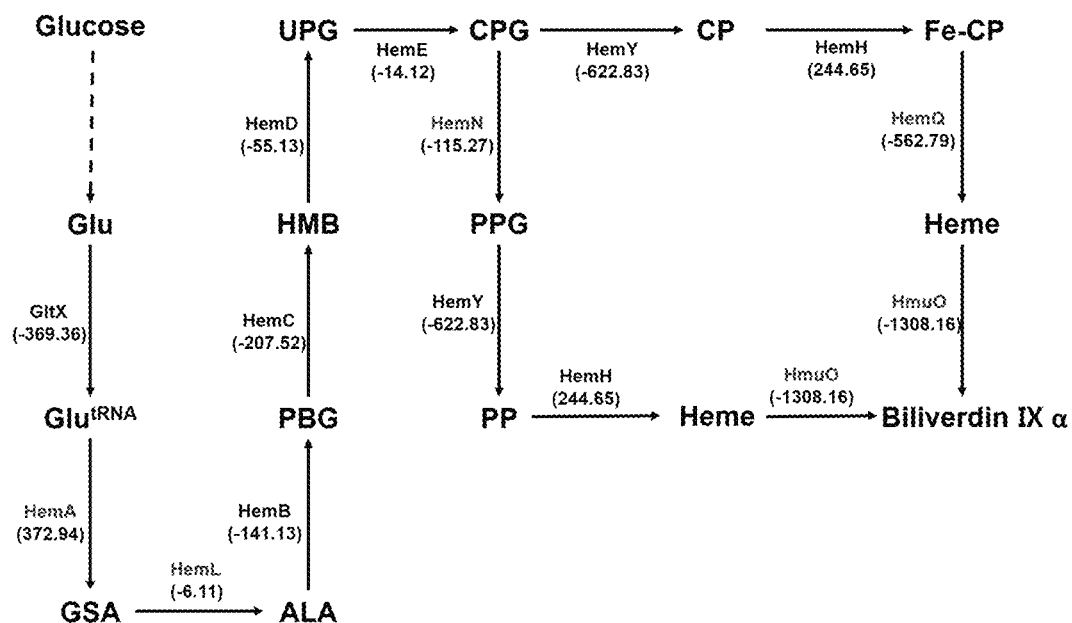
FIG. 1 shows the biosynthetic pathway and related enzymes for the production of biliverdin IX-alpha by *Corynebacterium glutamicum*, wherein the red represents an overexpressed enzyme and the parentheses represent the Gibbs free energy of each related enzyme.
Figure 2:
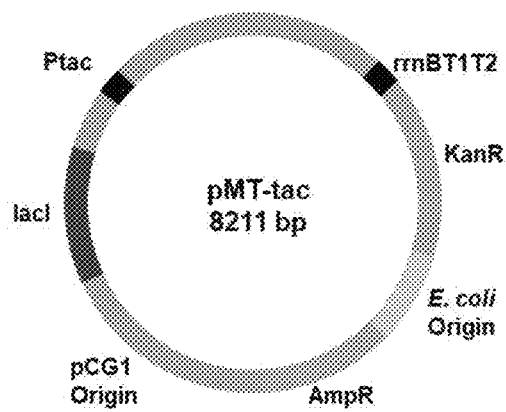
FIG. 2 shows a vector map of a *Corynebacterium glutamicum* overexpression recombinant vector (pMT1-tac)

The results are shown in FIG. 1, and the parentheses in FIG. 1 represent the change in Gibbs free energy of the reaction involving each enzyme. A positive Gibbs free energy change means a thermodynamically unstable nonspontaneous reaction. A negative Gibbs free energy change means a thermodynamically stable spontaneous reaction. Among them, the reaction involving the hemA gene, having the highest positive value, is predicted to be the most unstable nonspontaneous reaction on the biliverdin biosynthesis pathway, which means that it is the most important stage in improving biliverdin biosynthesis.

Example 2: Construction of Recombinant Vectors Having Target Genes (hemA, hemL) Inserted Therein Based on Result of Thermodynamic Stability Analysis A recombinant vector overexpressing the hemA gene was constructed based on the result of Example 1. The previous study (Korean Patent No. 10-1780767) has demonstrated the effects of co-overexpression of hemA and hemL genes. Thus, the following recombinant vector construction experiment was conducted to introduce both genes into the pEKEx2 vector. First, hemA and hemL genes were obtained through PCR using ALF and ALR (SEQ ID NOS: 7 and 8) and pMT-tac hemAL (Korean Patent Application No.: 10-2017-0061713) as a template. In order to construct a pEKEx2-hemAL vector (FIG. 5), the amplified hemAL gene was cleaved with the restriction enzyme PstI forming a sticky end at 5' and with the restriction enzyme SalI forming a sticky end at 3', and then inserted into the pEKEx2 vector cleaved with the same restriction enzymes.

Example 3: Construction of Overexpression Recombinant Vector for *Corynebacterium glutamicum* Transformation In order to remove the kanamycin-resistant gene from pMT-tac (produced in accordance with Korean Patent No. 10-1756338), the recombinant vector for *Corynebacterium glutamicum* transformation, the recombinant vector was cleaved with SalI, the restriction enzyme forming a sticky end at 5' and SnaBI, the restriction enzyme forming a sticky end at 3'. In order to utilize two compatible vectors in the *Corynebacterium glutamicum* strain, a zeocin-resistance gene was introduced into the conventional vector.

Figure 3:
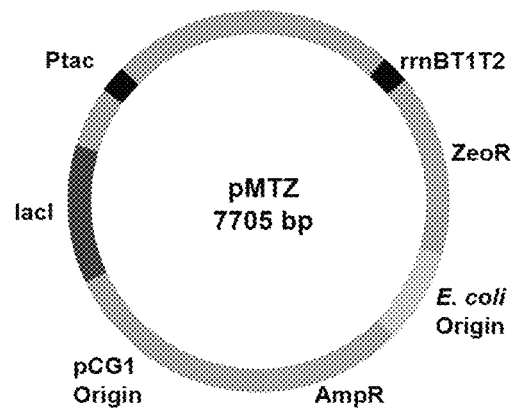
FIG. 3 shows a vector map of a *Corynebacterium glutamicum* overexpression recombinant vector (pMTZ); (a) to (c) of FIG. 4 show vector maps of *Corynebacterium glutamicum* HemN, HemQ and HmuO overexpression recombinant vectors (pMTZ-hemN, pMTZ-hemQ and pMTZ-hmuO)

The zeocin gene (SEQ ID NO: 6) was obtained by PCR using primers ZF and ZR (SEQ ID NOS: 9 and 10), cleaved with the restriction enzyme and inserted into pMT-tac to produce a recombinant vector pMTZ having the zeocin gene (FIG. 3). In order to determine whether or not can be used in conjunction with the pEKEx2 vector, the produced pMTZ recombinant vector was transformed into the *Corynebacterium glutamicum* strain (KCTC 3017) along with the pEKEx2 vector and pEKEx2-hemAL (FIG. 5), and the resulting strains were designated "KZ" and "ALZ".

TABLE 1

Primer sequences used in the present invention

| Primer name | Primer sequence | SEQ ID NO: |
|---|---|---|
| ALF | AATCTGCAGAAGGAGATATACATGAC CAAGAAGCTTTTAGCGC | 7 |
| ALR | ACTGTCGACTCACAACTTCGCAAACA CCC | 8 |
| ZF | CCCGTCGACGTTGACAATTAATCATC GGCATAG | 9 |
| ZR | ATTACGTAGTGTCAGTCCTGCTCCTC | 10 |
| NF | GGGATCGATATGTCAGTTTTTGGTGT GTATATTC | 11 |
| NR | CCCGCGGCCGCTTAGTCTTCTTCACT AAGCAAAATG | 12 |
| QF | CCCATCGATATGAGCGAGCTCGATAT TAAACAG | 13 |
| QR | CCAGCGGCCGCTTAAGGAAGAACCTT AATCAGATCTGCAATG | 14 |
| OF | GCGATCGATATGACAAGCATTATTGC AAGC | 15 |
| OR | GGGGGATCCTTAAGCAAGAGCCTGAA AAACTTGCTGATT | 16 |
| ALQF | GCCGGATCCAAGGAGATATAGATGAG CGAGCTCGATATTAAACAG | 17 |
| ALQR | CGCGGTACCTTAAGGAAGAACCTTAA TCAGATCTGC | 18 |

TABLE 1-continued

Primer sequences used in the present invention

| Primer name | Primer sequence | SEQ ID. NO: |
|---|---|---|
| ALOF | CCCGGATCCAAGGAGATATAGATGAC AAGCATTATTGCAAGCAACAG | 19 |
| ALOR | CCCGGTACCTTAAGCAAGAGCCTGAA AAACTTGCTG | 20 |
| QOF | CCCGCGGCCGCAAGGAGATATAGATG ACAAGCATTATTGCAAGCAA | 21 |
| QOR | GAGGCGGCCGCTTAAGCAAGAGCCTG AAAAACTTG | 22 |
| OQF | CCCGGATCCAAGGAGATATAGATGAG CGAGCTCGATATTAAACAGC | 23 |
| OQR | GGGGCGGCCGCTTAAGGAAGAACCTT AATCAGATCTGCAATGT | 24 |

Example 4: Production of Recombinant Strains Transformed with *Corynebacterium glutamicum*-Derived hemN and hemQ Genes Recombinant vectors including hemN and hemQ genes derived from *Corynebacterium glutamicum* were produced.

In order to clone the hemN gene (SEQ ID NO: 5) and the hemQ gene (SEQ ID NO: 3) derived from the *Corynebacterium glutamicum* strain into the *Corynebacterium glutamicum* overexpression recombinant vector pMTZ produced in Example 1, the primers NF (SEQ ID NO: 11), NR (SEQ ID NO: 12), QF (SEQ ID NO: 13) and QR (SEQ ID NO: 14), including the ClaI and NotI restriction enzyme sequence and the ClaI and NotI restriction enzyme sequence, respectively, were synthesized based on the base sequence. Then, PCR was performed using NF and NR, or QF and QR primers and using *Corynebacterium glutamicum* ATCC 13032 gDNA as a template to obtain a hemN gene and a hemQ gene, respectively.

Figure 4:
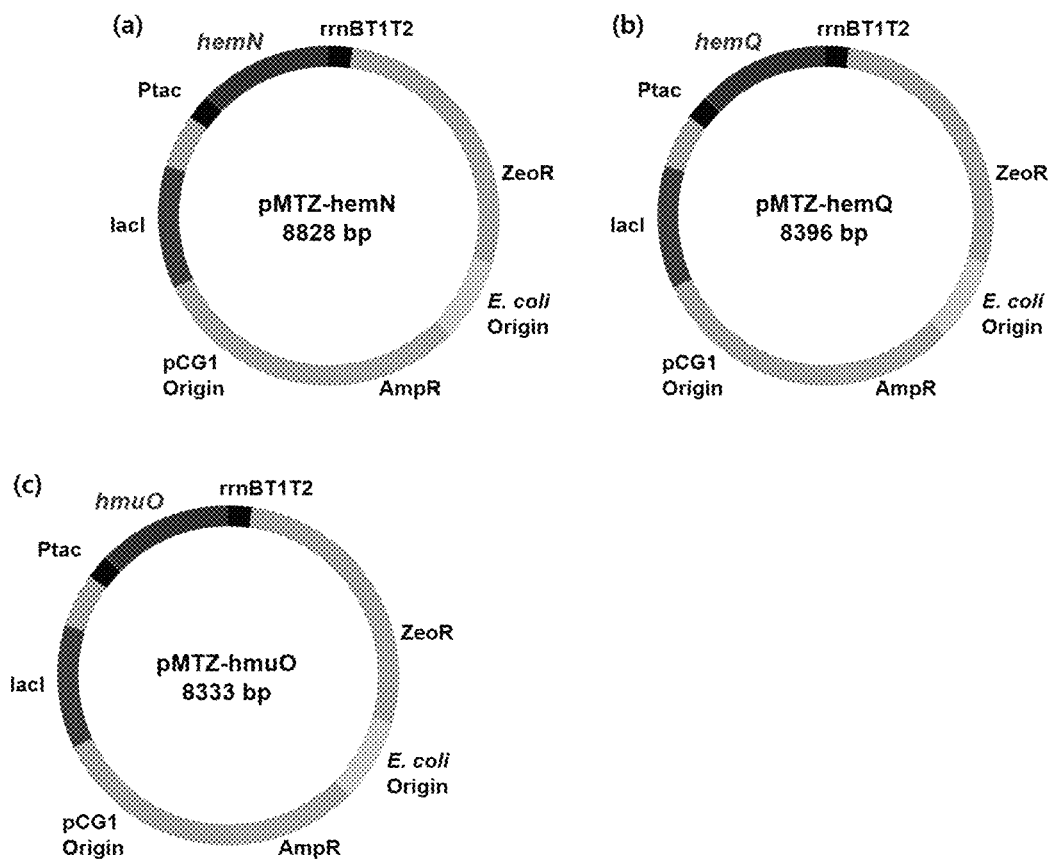

The PCR products including the pMTZ vector and each of the hemN gene and the hemQ gene thus obtained was treated with restriction enzymes to perform ligation reactions and then transformed into *E. coli* DH5a strains, and the constructed recombinant vectors were designated "pMTZ-hemN" and "pMTZ-hemQ" (FIG. 4). Together with the pEKEx2-hemAL vector, each of the pMTZ-hemN and pMTZ-hemQ were transformed into *Corynebacterium glutamicum* (KCTC 3017). The transformed *Corynebacterium glutamicum* KCTC 3017 strains were respectively designated "ALN" and "ALQ".

Example 5: Comparison of Heme Production Between Recombinant Strains

Heme production of KZ and ALZ strains, the recombinant strains produced in Example 3, and the ALN and ALQ strains produced in Example 4 were analyzed.

Each strain was cultured at 30° C. and 150 rpm for 60 hours in a 500 ml shaken Erlenmeyer flask containing 100 ml of CGX II medium (20 g $(NH_4)_2SO_4$, 5 g urea, 1 g $KH_2PO_4$, 1 g $K_2HPO_4$, 42 g 3-morpholinopropanesulfonic acid (MOPS), 0.25 g $MgSO_4.7H_2O$, 10 mg $CaCl_2$), 10 mg $FeSO_4.7H_2O$, 0.1 mg $MnSO_4.H_2O$, 1 mg $ZnSO_4.7H_2O$, 0.31 mg $CuSO_4.5H_2O$, 0.02 mg $NiCl_2.6H_2O$, and 0.2 mg biotin in 1 L of sterile distilled water).

The concentration of heme produced was analyzed via reverse-phase HPLC (Waters Corporation, USA) using a UV-detector/analyzer set to a wavelength of 400 nm, and the conditions were as follows. The analysis was carried out in a concentration gradient condition using a C18 column, and an initial solvent ratio was 20% Solvent A (1:9=methanol:acetonitrile) and 80% Solvent B (sterile distilled water containing 0.5% trifluoroacetic acid, titrated to pH 2.6) and a concentration gradient was generated for 40 minutes such that a final solvent ratio was 95% Solvent A and 5% Solvent B.

As shown in FIG. 7, the result showed that the ALQ strain transformed with the hemA gene, the hemL gene and the hemQ gene has the highest heme biosynthesis capability.

Example 6: Production of Recombinant Strains Transformed with *Corynebacterium glutamicum*-Derived hmuO Gene In order to clone the hmuO gene (SEQ ID NO: 4) derived from the *Corynebacterium glutamicum* strain into the recombinant vector pMTZ produced in Example 3, an OF primer (SEQ ID NO: 15) and an OR primer (SEQ ID NO: 16) including the ClaI and NotI restriction enzyme sequences were synthesized based on the base sequences. PCR was performed using the *Corynebacterium glutamicum* ATCC 13032 gDNA as a template PCR and using OF and OR primers to obtain the gene.

Each of the PCR product including the pMTZ vector and the hmuO gene was treated with a restriction enzyme to conduct the ligation reaction, and was then transformed into *E. coli* DH5a, and the constructed recombinant vector was designated "pMTZ-hmuO" (FIG. 4). The pMTZ-hmuO and pEKEx2-hemAL vectors were transformed into the *Corynebacterium glutamicum* strain (KCTC 3017). The transformed *Corynebacterium glutamicum* KCTC 3017 strain was designated "ALO".

Example 7: Determination of Biliverdin and Other Porphyrin Production Capability of ALO Strain The biliverdin and other porphyrin production of the ALO strain produced in Example 6 was determined. The transformants were cultured for 60 hours at 30° C. and 150 rpm in a 500 ml shaken Erlenmeyer flask containing 100 ml of CGXII medium.

The concentrations of produced heme and porphyrin byproduct were analyzed using reverse-phase HPLC (Waters Corporation, USA) including a UV-detector/analyzer set to a wavelength of 400 nm, and the conditions were as follows. The analysis was carried out in a concentration gradient condition using a C18 column, and an initial solvent ratio was 20% Solvent A (1:9=methanol:acetonitrile) and 80% Solvent B (sterile distilled water containing 0.5% trifluoroacetic acid, titrated to pH 2.6) and a concentration gradient was generated for 40 minutes such that the final solvent ratio became 95% Solvent A and 5% Solvent B.

The concentration of produced biliverdin was analyzed through reverse-phase HPLC (Waters Corporation, USA) including a UV-detector/analyzer set to a wavelength of 376 nm, and the conditions were as follows. The analysis was carried out in a concentration gradient condition using a C18 column and an initial solvent ratio was 25% Solvent C (methanol) and 75% Solvent D (1 M ammonium acetic acid, pH 5.16) and a concentration gradient was generated for 8 minutes such that a final solvent ratio became 95% Solvent C and 5% Solvent D. The ratio of 95:5 was maintained without a concentration gradient for 2 minutes, and a concentration gradient was generated for 8 minutes such that a final solvent ratio became 25% Solvent C and 75% Solvent D.

As shown in FIG. 8, the result showed that the *Corynebacterium glutamicum* recombinant strain ALO produced uroporphyrin III and coproporphyrin III, and heme as prophyrin by-products, and exhibited high biliverdin productivity. Protoporphyrin IX was not produced.

Example 8: Vector Modulation for Optimizing Biliverdin Production

In order to clone the hemQ gene (SEQ ID NO: 3) and the hmuO gene (SEQ ID NO: 4) derived from the *Corynebacterium glutamicum* strain into the *Corynebacterium glutamicum* recombinant vector pEKEx2-hemAL (FIG. 5), the ribosomal binding site was inserted in front of each gene, ALQF (SEQ ID NO: 17), ALQR (SEQ ID NO: 18), ALOF (SEQ ID NO: 19) and ALOR (SEQ ID NO: 20), as the primers including BamHI and KpnI restriction enzyme sequences, were synthesized, and PCR was performed using the *Corynebacterium glutamicum* ATCC 13032 gDNA as a template using the ALQF and ALQR, or ALOF and ALOR primers to obtain the genes.

PCR products including the pEKEx2-hemAL vector, the hemQ gene and the hmuO gene were each treated with restriction enzymes to perform ligation reactions and transformed into the *E. coli* DH5a strain. The constructed recombinant vectors were designated "pEKEx2-hemALQ" and "pEKEx2-hemALO", respectively (FIG. 6). Each vector was transformed together with the pMTZ-hmuO vector produced in Example 6 into the *Corynebacterium glutamicum* strain (KCTC 3017). The transformed *Corynebacterium glutamicum* KCTC 3017 strains were designated "BVMOD1" and "BVMOD2", respectively.

Meanwhile, in order to clone the hemQO gene derived from the *Corynebacterium glutamicum* strain into the *Corynebacterium glutamicum* overexpression recombinant vector pMTZ, QF and QR primers including ClaI and NotI restriction enzyme sequences were synthesized for the hemQ gene (SEQ ID NO: 3). Based on the base sequence of the hmuO gene (SEQ ID NO: 4), for hmuO, a ribosome-binding site was inserted in front of the gene, and the primers QOF (SEQ ID NO: 21) and QOR (SEQ ID NO: 22), including the NotI and NotI restriction enzyme sequences, were synthesized. Then, PCR was performed using the synthesized primers to obtain the gene.

The pMTZ vector produced in Example 3 and the hemQO gene were treated with restriction enzymes to conduct ligation reaction and then transformed into an *E. coli* DH5a strain. The constructed recombinant vector was designated "pMTZ-hemQO" (see FIG. 6C). The pMTZ-hemQO was transformed together with the pEKEx2-hemAL vector into the *Corynebacterium glutamicum* strain (KCTC 3017). The transformed *Corynebacterium glutamicum* KCTC 3017 strain was designated "BVMOD3".

In order to clone the hemOQ gene derived from the *Corynebacterium glutamicum* strain into the recombinant vector pMTZ, OF and OR primers including ClaI and BamHI restriction enzyme sequences for the hmuO gene (SEQ ID NO: 4) were synthesized. In the case of the hemQ gene (SEQ ID NO: 3), the ribosome-binding site was inserted in front of the gene, and primers OQF (SEQ ID NO: 23) and OQR (SEQ ID NO: 24) including the BamHI and NotI restriction enzyme sequences were synthesized. Then, PCR was performed using the synthesized primers to secure genes.

The pMTZ vector produced in Example 3 and the hemOQ gene were treated with restriction enzymes to conduct a ligation reaction and were then transformed into the *Escherichia coli* DH5a strain. The constructed recombinant vector was designated "pMTZ-hemOQ". The pMTZ-hemOQ was transformed together with the pEKEx2-hemAL vector into *Corynebacterium glutamicum* (KCTC 3017). The transformed *Corynebacterium glutamicum* KCTC 3017 strain was designated "BVMOD4".

Example 9: Comparison of Biliverdin Production Capability Between Modulated Recombinant Strains The biliverdin production capability was compared between the BVMODD1, BVMOD2, BVMOD3 and BVMOD4 strains obtained in Example 8. Each transformant was incubated for 60 hours at 30° C. and 150 rpm in a 500 ml shaken Erlenmeyer flask containing 100 ml of a CGXII medium (the same as above).

As shown in FIG. 9, the result showed that all of BVMODD1, BVMOD2, BVMOD3 and BVMOD4 strains have heme and biliverdin production capability and that BVMODD1, BVMOD2 and BVMOD3 strains showed high biliverdin production capability, and in particular, the BVMOD3 strain exhibited the highest biliverdin production capability. The BVMOD4 strain exhibited considerably superior heme production capability and lower biliverdin production capability than other strains.

Example 10: Biliverdin Production Through Fed-Batch Fermentation

The BVMOD3 strain showing the highest biliverdin production capability in Example 9 was selected and was fed-batch fermented in a 5 L incubator. The BVMOD3 strain was cultured at an initial temperature of 30° C., 1.8 vvm and 600 rpm using 1.8 L of a CGXII medium. Strain growth was measured using a spectrophotometer and the glucose content was analyzed using a glucose analysis kit (Sigma Aldrich). The initial glucose content was 80 g/L and a 50% glucose solution was added when the glucose concentration fell below 15 g/L.

As shown in FIG. 10, the result showed that, when the recombinant strain was fed-batch cultured, 70 mg/L of biliverdin IX-alpha were produced in 72 hours of culture.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The recombinant strain according to the present invention is capable of synthesizing biliverdin IX-alpha in an environmentally friendly manner using only glucose without the addition of any nitrogen source, thus replacing the synthesis of biliverdin IX-alpha through chemical treatment, which is a conventional synthetic method causing environmental pollution problems.

What is claimed is:

1. A recombinant strain of a genus *Corynebacterium* having capability to produce biliverdin IX-alpha, wherein a hemA gene comprising the nucleotide sequence of SEQ ID NO:1 and a hemL gene comprising the nucleotide sequence of SEQ ID NO:2 are amplified, and wherein a hemQ gene comprising the nucleotide sequence of SEQ ID NO:3 or a hmuO gene comprising the nucleotide sequence of SEQ ID NO:4 is introduced by a recombinant vector in a form of hemQ or hmuO.

2. A method of producing biliverdin IX-alpha comprising:
(a) producing the biliverdin IX-alpha by culturing the recombinant strain of the genus *Corynebacterium* according to claim 1; and
(b) recovering the produced biliverdin IX-alpha.

3. A recombinant strain of a genus *Corynebacterium* having capability to produce biliverdin IX-alpha, wherein a hemA gene comprising the nucleotide sequence of SEQ ID NO:1, a hemL gene comprising the nucleotide sequence of SEQ ID NO:2, a hemQ gene comprising the nucleotide sequence of SEQ ID NO:3, and hmuO gene comprising the nucleotide sequence of SEQ ID NO:4, are amplified, and wherein the hemQ gene and the hmuO gene are introduced by a recombinant vector in a form of hemQO, in which the hemQ gene is located in front of the hmuO gene in the recombinant vector.

4. A method of producing a biliverdin IX-alpha comprising:
   (a) producing the biliverdin IX-alpha by culturing the recombinant strain of the genus *Corynebacterium* according to claim 3; and
   (b) recovering the produced biliverdin IX-alpha.

* * * * *